US007794751B2

(12) United States Patent
Chudzik et al.

(10) Patent No.: US 7,794,751 B2
(45) Date of Patent: Sep. 14, 2010

(54) MEDICAMENT INCORPORATION MATRIX

(75) Inventors: Stephen J. Chudzik, St. Paul, MN (US); Terrence P. Everson, Eagan, MN (US); Richard A. Amos, St. Anthony, MN (US)

(73) Assignee: SurModics, Inc., Eden Prairie, MN (US)

( * ) Notice: Subject to any disclaimer, the term of this patent is extended or adjusted under 35 U.S.C. 154(b) by 949 days.

(21) Appl. No.: 11/387,508

(22) Filed: Mar. 23, 2006

(65) Prior Publication Data

US 2006/0165751 A1 Jul. 27, 2006

Related U.S. Application Data

(62) Division of application No. 09/901,425, filed on Jul. 9, 2001, now Pat. No. 7,056,533.

(60) Provisional application No. 60/225,465, filed on Aug. 15, 2000.

(51) Int. Cl.
*A61K 9/14* (2006.01)
(52) U.S. Cl. ........................................ 424/487
(58) Field of Classification Search ................. 424/487
See application file for complete search history.

(56) References Cited

U.S. PATENT DOCUMENTS

| | | | |
|---|---|---|---|
| 3,622,546 A | 11/1971 | Engelhardt et al. | |
| 3,767,398 A | 10/1973 | Morgan | |
| 4,107,121 A | 8/1978 | Stoy | 260/29.6 |
| 4,260,538 A | 4/1981 | Iseler et al. | |
| 4,304,591 A | 12/1981 | Mueller et al. | |
| 4,401,793 A | 8/1983 | Chiao et al. | |
| 4,442,133 A | 4/1984 | Greco | 427/2 |
| 4,499,251 A | 2/1985 | Omura et al. | |
| 4,533,723 A | 8/1985 | Weitemeyer | |
| 4,655,771 A | 4/1987 | Wallsten | 623/1 |
| 4,733,665 A | 3/1988 | Palmaz | 606/108 |
| 4,778,786 A | 10/1988 | Reever et al. | |
| 4,800,882 A | 1/1989 | Gianturco | 128/343 |
| 4,806,381 A | 2/1989 | Engelbrecht et al. | |
| 4,886,062 A | 12/1989 | Wiktor | 128/343 |
| 4,895,566 A | 1/1990 | Lee | 604/266 |
| 4,917,686 A | 4/1990 | Bayston | 604/265 |
| 4,933,182 A | 6/1990 | Higashi et al. | |
| 4,952,402 A | 8/1990 | Sparks et al. | |
| 4,952,419 A | 8/1990 | De Leon | 427/2 |
| 4,954,126 A | 9/1990 | Wallsten | 600/36 |
| 5,002,582 A | 3/1991 | Guire | 623/66 |
| 5,013,306 A | 5/1991 | Solomon | 604/264 |
| 5,015,479 A | 5/1991 | Mulligan et al. | |
| 5,019,096 A | 5/1991 | Fox, Jr. et al. | |
| 5,043,167 A | 8/1991 | Rotini et al. | |
| 5,061,275 A | 10/1991 | Wallsten | 623/1 |
| 5,114,719 A | 5/1992 | Sabel et al. | |
| 5,120,548 A | 6/1992 | McClelland et al. | |
| 5,128,142 A | 7/1992 | Mulligan et al. | |
| 5,152,758 A | 10/1992 | Kaetsu et al. | |
| 5,169,642 A | 12/1992 | Brinker et al. | |
| 5,214,493 A | 5/1993 | Sugiyama et al. | |
| 5,268,182 A | 12/1993 | Brinker et al. | |
| 5,270,358 A | 12/1993 | Asmus | |
| 5,304,621 A | 4/1994 | Staiger et al. | |
| 5,316,774 A | 5/1994 | Eury et al. | |
| 5,374,661 A | 12/1994 | Betlach, II | |
| 5,443,455 A | 8/1995 | Hergenrother | 428/380 |
| 5,447,724 A | 9/1995 | Helmus et al. | |
| 5,455,046 A | 10/1995 | Baichwal | |
| 5,464,650 A | 11/1995 | Berg et al. | |
| 5,512,055 A | 4/1996 | Domb et al. | |
| 5,525,348 A | 6/1996 | Whitbourne et al. | |
| 5,556,635 A | 9/1996 | Istin | 424/448 |
| 5,602,197 A | 2/1997 | Johnson et al. | |
| 5,607,417 A | 3/1997 | Batich et al. | |
| 5,624,411 A | 4/1997 | Tuch | |
| 5,667,801 A | 9/1997 | Baichwal | |
| 5,674,511 A | 10/1997 | Kacher et al. | |
| 5,674,521 A | 10/1997 | Gehrke et al. | |

(Continued)

FOREIGN PATENT DOCUMENTS

EP 0073890 3/1983

(Continued)

OTHER PUBLICATIONS

CL. Bell, and N. A. Peppas, *J. Biomater. Sci. Polymer Edn.* 7(8):671-683 (1996) and C.L. Bell.
Brzoska, J.B., et. al., *Langmuir* 10:4367-4373, 1994.
N. A. Peppas, *Biomaterials* 17:1203-1218 (1996).
Scott, et al., *Biomaterials* 20(15):1371-1380 (1999).
Mathur, et al., *J. Controlled Release* 54(2):177-184 (1998).
Solomon, D. D. And Sherertz, R. J., *J. Controlled Release,* 6:343-352 (1987).
Peppas N.A., et al., "Poly(ethylene Glycol)-Containing Hydrogels in Drug Delivery", *Journal of Controlled Release,* Elsevier Science Publishers B. V, Amsterdam, NL, vol. 62, No. 1/2, (1999), pp. 81-87.
Bell, Cristi L. et al., "Water, solute and protein diffusion in physiologically responsive hydrogels of poly(methacrylic acid-g-ethylene glycol)", *Biomaterials 17* 1996, 1203-1218.
Chetoni, P. et al., "Silicone rubber/hydrogel composite ophthalmic inserts: preparation and preliminary in vitro/in vivo evaluation", *Eur J. Pharm Biopharm, 46(1): 125-32* Jul. 1998, 1 page Abstract.

(Continued)

*Primary Examiner*—Raymond J Henley, III
(74) *Attorney, Agent, or Firm*—Pauly, Devries Smith & Deffner, L.L.C.

(57) ABSTRACT

A coating composition, in both its uncrosslinked and crosslinked forms, for use in delivering a medicament from the surface of a medical device positioned in vivo. Once crosslinked, the coating composition provides a gel matrix adapted to contain the medicament in a form that permits the medicament to be released from the matrix in a prolonged, controlled, predictable and effective manner in vivo. A composition includes a polyether monomer, such as an alkoxy poly(alkylene glycol), a carboxylic acid-containing monomer, such as (meth)acrylic acid, a photoderivatized monomer, and a hydrophilic monomer such as acrylamide.

49 Claims, No Drawings

U.S. PATENT DOCUMENTS

| | | | |
|---|---|---|---|
| 5,702,717 A | 12/1997 | Cha et al. | |
| 5,707,366 A | 1/1998 | Solomon et al. | |
| 5,739,210 A | 4/1998 | Scranton | 525/279 |
| 5,749,837 A | 5/1998 | Palermo | 600/585 |
| 5,756,145 A | 5/1998 | Darouiche | |
| 5,769,796 A | 6/1998 | Palermo | 600/585 |
| 5,773,025 A | 6/1998 | Baichwal | |
| 5,844,039 A | 12/1998 | Scranton | 524/530 |
| 5,853,745 A | 12/1998 | Darouiche | 424/423 |
| 5,884,039 A | 3/1999 | Ludwig | 395/200.57 |
| 5,939,090 A | 8/1999 | Beaurline et al. | |
| 5,965,505 A | 10/1999 | Baillely et al. | |
| 5,997,517 A | 12/1999 | Whitbourne | 604/265 |
| 6,004,573 A | 12/1999 | Rathi et al. | |
| 6,042,875 A | 3/2000 | Ding | 427/2.24 |

FOREIGN PATENT DOCUMENTS

| | | |
|---|---|---|
| EP | 0115410 | 8/1984 |
| EP | 0747069 | 12/1996 |
| GB | 1184763 | 3/1970 |
| GB | 1390711 | 4/1975 |
| WO | WO-94/16646 | 8/1994 |
| WO | WO-97/10011 | 3/1997 |
| WO | WO 99/47129 | 9/1999 |
| WO | WO 99/47176 | 9/1999 |
| WO | WO 01/21326 | 3/2001 |
| WO | WO-02/13871 | 2/2002 |

OTHER PUBLICATIONS

Garrett, Q. et al., "Human serum albumin adsorption on hydrogel contact lenses in vitro", *Invest Ophthalmol Vis Sci, 37(13):2594-602* Dec. 1996, 1 page Abstract.

Hemmer, W. et al., "Allergic contact dermatitis to artificial fingernails prepared from UV light-cured acrylates", *J Am Acad Dermatol. 35(3 Pt 1): 377-80* Sep. 1996, 1 page Abstract.

Sofia, S. J. et al., "Grafting of PEO to polymer surfaces using electron beam irradiation", *J Biomed Mater Res. 40(1):153-63* Apr. 1998, 1 page Abstract.

Wu, Xy et al., "Expression of integrin and organization of F-actin in epithelial cells depends on the underlying surface", *Invest Ophthalmol Vis Sci. 35(3):878- 90* Mar. 1994, 1 page Abstract.

MEDICAMENT INCORPORATION MATRIX

CROSS REFERENCE TO RELATED APPLICATION

The present application is a divisional of U.S. patent application Ser. No. 09/901,425, filed Jul. 9. 2001, now U.S. Pat. No. 7,056,533 which itself claims the benefit of provisional U.S. patent application filed 15 Aug. 2000 and assigned Ser. No. 60/225,465, the entire disclosure of each of which is incorporated herein by reference.

GOVERNMENT FUNDING

The United States government may have certain rights in this invention by virtue of NIH Grant No. 1 R43 AR 44758-01.

TECHNICAL FIELD

In one aspect, the present invention relates to the delivery of medicaments, such as drugs, from within or upon the surface of implantable medical devices. In another aspect, the invention relates to hydrogel matrices containing these and other medicaments.

BACKGROUND OF THE INVENTION

Hydrogels are typically described as hydrophilic polymer networks that are capable of absorbing large amounts of water, yet are themselves insoluble because of the presence of physical or chemical crosslinks, entanglements or crystalline regions. Hydrogels have found extensive use in biomedical applications, including as coatings and drug delivery systems. Hydrogels are often sensitive to the conditions of their surrounding environment, such that the swelling ratio of the materials can be affected by temperature, pH, ionic strength and/or the presence of a swelling agent. Several parameters can be used to define or characterize hydrogels, including the swelling ratio under changing conditions, the permeability coefficient of certain solutes, and the mechanical behavior of the hydrogel under conditions of its intended use. When used as drug delivery systems these changes in the environment can often be controlled or predicted in order to regulate drug release. (See Bell and Peppas, cited below).

A particular type of hydrogel that has been described in recent years involves the combination of poly(methacrylic acid) ("PMAA") backbones and polyethylene glycol ("PEG") grafts. For instance, Mathur, et al., *J. Controlled Release* 54(2):177-184 (1998) describe "responsive" hydrogel networks of this type. The hydrogels exhibit swelling transitions, in various solvent systems, and in response to external stimuli. These transitions, in turn, can lead to the formation or disruption of hydrogen-bonded complexes between the backbone and graft portions. The article describes the role of hydrophobic interactions in stabilizing the complexes.

A variety of references further describe the preparation and use of hydrogels for the delivery of medicaments, including those hydrogels based on the combination of polyalkylene glycols and poly(meth)acrylates. See, for instance, U.S. Pat. Nos. 5,884,039 and 5,739,210, which describe polymers having reversible hydrophobic functionalities, e.g., polymers having Lewis acid and Lewis base segments. The segments are hydrophilic and will either swell or dissolve in water. When incorporated into a polymer, the segments form water-insoluble or hydrophobic complexes. Upon changes in pH, temperature or solvent type, the complexes can dissociate, giving large transitions in viscosity, emulsification ability and mechanical strength. The polymers are said to be useful as reversible emulsifiers, super-absorbing resins, or as coatings for pharmaceutical agents.

See also, Scott, et al., *Biomaterials* 20(15):1371-1380 (1999), which describes the preparation of ionizable polymer networks prepared from oligo(ethylene glycol) multiacrylates and acrylic acid using bulk photopolymerization techniques. The networks are described for use in the preparation of controlled release devices for solutes.

Finally, C. L. Bell, and N. A. Peppas, *J. Biomater. Sci. Polymer Edn.* 7(8):671-683 (1996) and C. L. Bell and N. A. Peppas, *Biomaterials* 17:1203-1218 (1996) each describe the synthesis and properties of grafted P(MAA-g-EG) copolymers. The copolymers permit the reversible formation of complexes under appropriate conditions due to hydrogen bonding between the carboxylic acid groups of the PMAA and the oxygen atoms of the PEG chains, resulting in pH-sensitive swelling behavior. Complexation occurs at low pH, resulting in increased hydrophobicity in the polymer network. At higher pH values, the acid groups become ionized and the hydrogen bonding breaks down. The papers studied this pH sensitive swelling behavior in relation to the use of such materials in controlled release drug delivery and bio-separations.

The Bell and Peppas papers exemplified the swelling behavior of P(MAA-g-EG) samples containing 40:60, 50:50 and 60:40 ratios (weight percent) of PMAA:PEG, using PEG grafts having molecular weights of 200, 400 and 1000. The resultant hydrogels were evaluated by several means, including mechanical testing to determine shear modulus. The authors found that as the molecular weight of the PEG graft was increased, the modulus of the networks decreased in both the complexed and uncomplexed state.

When used for drug delivery, the materials prepared by Bell and Peppas were typically used as free standing hydrogel membranes, with no mention of their use upon a surface, let alone the surface of an implanted medical device. Nor, in turn, do these references provide any suggestion of the manner in which such matricies might be applied to any such surface.

Those references that do describe the delivery of medicaments from implanted devices tend to rely on approaches quite different from implanted hydrogels. The continuing development and use of implantable medical devices has led to the corresponding development of a variety of ways to deliver antibiotics and/or antiseptics to the implant site, in order to prevent potential infections associated with such devices.

For instance, a significant percent of fracture fixation devices (pins, nails, screws, etc.) and orthopedic joint implants become infected. Cure of infected orthopedic implants, such as joint prostheses, usually requires both removal of the prosthesis and administration of a long course of antibiotics. In most cases, this is followed by re-implantation of a new joint prosthesis weeks or months later, after making sure that the infection has been eradicated.

As described in the patents to Darouiche, cited below, considerable amount of attention and study has therefore been directed toward preventing colonization of bacterial and fungal organisms on the surfaces of orthopedic implants by the use of antimicrobial agents, such as antibiotics, bound to the surface of the materials employed in such devices. The objective of such attempts has been to produce a sufficient bacteriostatic or bactericidal action to prevent colonization.

Various methods have previously been employed to coat the surfaces of medical devices with an antibiotic. For example, one method involves applying or absorbing to the surface of the medical device a layer of surfactant, such as tridodecylmethyl ammonium chloride ("TDMAC") followed by an antibiotic coating layer.

A further method known to coat the surface of medical devices with antibiotics involves first coating the selected surfaces with benzalkonium chloride followed by ionic bonding of the antibiotic composition. See, e.g., Solomon, D. D. and Sheretz, R. J., *J. Controlled Release,* 6:343-352 (1987) and U.S. Pat. No. 4,442,133. Yet other methods of coating surfaces of medical devices with antibiotics are taught in U.S. Pat. No. 4,895,566 (a medical device substrate carrying a negatively charged group having a pK of less than 6 and a cationic antibiotic bound to the negatively charged group); U.S. Pat. No. 4,917,686 (antibiotics are dissolved in a swelling agent which is absorbed into the matrix of the surface material of the medical device); U.S. Pat. No. 4,107,121 (constructing the medical device with ionogenic hydrogels, which thereafter absorb or ionically bind antibiotics); U.S. Pat. No. 5,013,306 (laminating an antibiotic to a polymeric surface layer of a medical device); and U.S. Pat. No. 4,952,419 (applying a film of silicone oil to the surface of an implant and then contacting the silicone film bearing surface with antibiotic powders).

See also Ding et al., (U.S. Pat. No. 6,042,875), which describes a coating that permits timed or prolonged pharmacological activity on the surface of medical devices through a reservoir concept. Specifically, the coating comprises at least two layers: an outer layer containing at least one drug-ionic surfactant complex overlying a reservoir layer or tie layer containing a polymer and the drug which is substantially free of an ionic surfactant. Upon exposure to body tissue of a medical device covered with such coating, the ionically complexed drug in the outer layer is released into body fluid or tissue. Following release of such complexed drug, the ionic surfactant complex sites in the outer layer are left vacant.

After insertion of a medical device such as an orthopedic implant, the antibiotics and/or antiseptics quickly leach from the surface of the device into the surrounding environment. Over a relatively short period of time, the amount of antibiotics and/or antiseptics present on the surface decreases to a point where the protection against bacterial and fungal organisms is no longer effective. Furthermore, during implantation of orthopedic fracture fixation devices, such as intramedullary nails and external fixation pins, much of the antimicrobial coating sloughs off due to grating of the coated implant against the bone during insertion of the implant.

Hence, for some implants, and particularly those that both remain in the body for extended periods of time and that undergo tortuous processing in the course of their implantation or use, medicament coatings continue to be sought to provide improved durability.

U.S. Pat. No. 5,853,745 (Darouiche), describes a durable antimicrobial coated orthopedic device or other medical implant having a durable material layer that decreases the rate of leaching of antimicrobial agents into the surrounding environment. The patent provides an antimicrobial coated medical implant or orthopedic device having mechanical resiliency to minimize or avoid sloughing of the antimicrobial layer from the device during insertion. The medical implant has one or more of its surfaces coated with a composition comprising an antimicrobial coating layer comprising an antimicrobial agent in an effective concentration to inhibit the growth of bacterial and fungal organisms, and a protective coating layer formed over said antimicrobial coating layer.

When used as drug release coatings on devices, however, the various systems described above suffer from several drawbacks, e.g., in terms of the thickness of the coatings necessary to provide suitable amounts of drug, the kinetics (e.g., overall period of release), and the durability or tenacity of the coating itself. In spite of the various attempts and progress made to date, it remains clear that the need for a coating composition that provides an optimal combination of such properties as coating thickness, drug release profile, durability, swellability, generic applicability, and surface independence remains unmet.

Improved coatings for use on implanted devices, in order to provide medicament release in situ, are clearly needed.

SUMMARY OF THE INVENTION

The present invention provides a crosslinkable coating composition, in both its uncrosslinked and crosslinked forms, for use in delivering a medicament from the surface of a medical device positioned in vivo. Once crosslinked, the coating composition provides a gel matrix adapted to contain the medicament in a form that permits the medicament to be released from the matrix in a prolonged, controlled, predictable and effective manner in vivo. The combination of gel matrix and medicament can be provided in any suitable manner and at any suitable time, e.g., the medicament can be included in one or more components of the uncrosslinked composition and/or it can be incorporated into the formed or forming matrix, e.g., at the time of use, and before, during, or after crosslinking the composition or implanting the thus-coated device into a tissue site. When applied as a coating to the surface of a medical device, a gel matrix can be formed thereon by a process that includes a complexation reaction between carboxylic acid groups and ether groups. The complexation reaction serves to both improve the durability and tenacity of the coating and prolong the delivery of the medicaments incorporated into the matrix.

In a preferred embodiment, the coating composition preferably comprises a polymeric reagent formed by the polymerization of the following monomers:

a) about 1 to about 20 mole % of a polyether monomer, b) about 5 to about 75 mole % of a carboxylic acid-containing monomer, such that the effective ratio of ether groups to carboxylic acid groups in the resultant copolymer is between about 1 to 1 and about 10 to 1, c) optionally, about 0.1 to about 10 mole % of a photo-derivatized monomer, and d) an amount of a hydrophilic monomer suitable to bring the composition to 100% (e.g., about 0 to about 93.9 mole % of a hydrophilic monomer).

When the polymeric reagent is applied as a coating to the surface of a medical device, noncovalent interactions occur between carboxylic acid groups and ether groups, thus contributing to the formation of a gel matrix. The application of UV light provides photochemical attachment to the substrate as well as the formation of covalent crosslinks within the matrix. The matrix, thus formed, provides both improved durability and tenacity of the coating in a manner that prolongs the delivery of the medicaments incorporated into the matrix.

In a particularly preferred embodiment, for instance, the uncrosslinked composition comprises a polymeric reagent formed by the polymerization of the following monomers:

a) methoxy poly(ethylene glycolmethacrylate) ("methoxyPEGMA"), as the polyether monomer, in an amount of between about 5 and about 15 mole %, b) (meth)acrylic acid, as the carboxylic acid-containing monomer component, present in an amount of between about 30 and about 50 mole %, c) photoderivatized monomer, present in an amount of between about 1 to about 7 mole %, and d) acrylamide monomer, as a hydrophilic monomer, present in an amount of between about 30 and about 70 mole %.

Without intending to be bound by theory, it is believed that upon application of a solution of the uncrosslinked composition to the surface of a medical device, and UV illumination to activate the photogroups, that a covalently bound matrix is thus formed on the surface of the device. This matrix contains both carboxylic acid groups and ether groups which, under the appropriate conditions, form complexes. These complexes, in turn, increase the hydrophobicity of the matrix and appear to improve the durability and tenacity of the matrix, and prolong the release of the medicaments incorporated into the matrix.

A matrix of this invention provides an optimal and improved combination of such properties as medicament release profile, durability, tenacity, solubility, swellability, and coating thickness. Such a matrix can be used with a wide range of surface materials and configurations, and in turn, is widely applicable and useful with a variety of implanted devices.

DETAILED DESCRIPTION

The composition of this invention preferably includes between about 1 and about 20 mole % of a polyether monomer and preferably from about 5 to about 15 mole %. Most preferably, the polyether monomer is used at a final concentration of about 8 to about 12 mole %. The term "mole %" as used herein will be determined by the molecular weight of the monomer components.

The polyether monomer is preferably of the group of molecules referred to as alkoxy (poly)alkyleneglycol (meth)acrylates. The alkoxy substituents of this group may be selected from the group consisting of methoxy, ethoxy, propoxy, and butoxy. The (poly)alkylene glycol component of the molecule may be selected from the group consisting of (poly) propylene glycol and (poly)ethylene glycol. The (poly)alkylene glycol component preferably has a nominal weight average molecular weight ranging from about 200 g/mole to about 2000 g/mole, and ideally from about 800 g/mole to about 1200 g/mole. Examples of preferred polyether monomers include methoxy PEG methacrylates, PEG methacrylates, and (poly)propylene glycol methacrylates. Such polyether monomers are commercially available, for instance, from Polysciences, Inc., (Warrington, Pa.).

A composition of this invention preferably includes between about 5 to about 75 mole % of a carboxylic acid-containing monomer, such that the effective ratio of ether groups to carboxylic acid groups in the resultant copolymer is between about 1 to 1 and about 10 to 1. Preferred concentrations of the carboxylic acid-containing monomer are between about 30 to about 50 mole %. Most preferably, the carboxylic acid-containing monomer is used at a concentration between about 30 to about 40 mole %. These monomers can be obtained commercially, for instance, from Sigma-Aldrich, Inc. (St. Louis, Mo.).

Preferred carboxylic acid-containing monomers are selected from carboxyl substituted ethylene compounds, also known as alkenoic acids. Examples of particularly preferred carboxylic acid-containing monomers include acrylic, methacrylic, maleic, crotonic, itaconic, and citraconic acid. Most preferred examples of carboxylic acid-containing monomers include acrylic acid and methacrylic acid.

A composition of the present invention preferably includes between about 0.1 and about 10 mole % of a photoderivatized monomer, more preferably between about 1 and about 7 mole %, and most preferably between about 3 and about 5 mole %.

Examples of suitable photoderivatized monomers are ethylenically substituted photoactivatable moieties which include N-[3-(4-benzoylbenzoamido)propyl]methacrylamide ("BBA-APMA"), 4(2-acryloxyethoxy)-2-hydroxybenzophenone, 4-methacryloxy-2-hydroxybenzophenone, 4-methacryloxy-2-hydroxybenzophenone, 9-vinyl anthracene, and 9-anthracenylmethyl methacrylate. An example of a preferred photoderivatized monomer is BBA-APMA.

Photoreactive species are defined herein, and preferred species are sufficiently stable to be stored under conditions in which they retain such properties. See, e.g., U.S. Pat. No. 5,002,582, the disclosure of which is incorporated herein by reference. Latent reactive groups can be chosen that are responsive to various portions of the electromagnetic spectrum, with those responsive to ultraviolet and visible portions of the spectrum (referred to herein as "photoreactive") being particularly preferred.

Photoreactive species respond to specific applied external stimuli to undergo active specie generation with resultant covalent bonding to an adjacent chemical structure, e.g., as provided by the same or a different molecule. Photoreactive species are those groups of atoms in a molecule whose covalent bonds remain unchanged under conditions of storage but upon activation by an external energy source, form covalent bonds with other molecules.

The photoreactive species generate active species such as free radicals and particularly nitrenes, carbenes, and excited states of ketones upon absorption of electromagnetic energy. Photoreactive species can be chosen to be responsive to various portions of the electromagnetic spectrum, and photoreactive species that are responsive to, e.g., ultraviolet and visible portions of the spectrum, are preferred and can be referred to herein occasionally as "photochemical group" or "photogroup."

The photoreactive species in photoreactive aryl ketones are preferred, such as acetophenone, benzophenone, anthraquinone, anthrone, and anthrone-like heterocycles, i.e., heterocyclic analogs of anthrone such as those having N, O, or S in the 10-position, or their substituted, e.g., ring substituted, derivatives. Examples of preferred aryl ketones include heterocyclic derivatives of anthrone, including acridone, xanthone, and thioxanthone, and their ring substituted derivatives. Particularly preferred are thioxanthone, and its derivatives, having excitation energies greater than about 360 nm.

The functional groups of such ketones are preferred since they are readily capable of undergoing the activation/inactivation/reactivation cycle described herein. Benzophenone is a particularly preferred photoreactive moiety, since it is capable of photochemical excitation with the initial formation of an excited singlet state that undergoes intersystem crossing to the triplet state. The excited triplet state can insert into carbon-hydrogen bonds by abstraction of a hydrogen atom (from a support surface, for example), thus creating a radical pair. Subsequent collapse of the radical pair leads to formation of a new carbon-carbon bond. If a reactive bond (e.g., carbon-hydrogen) is not available for bonding, the ultraviolet light-induced excitation of the benzophenone group is reversible and the molecule returns to ground state energy level upon removal of the energy source. Photoactivatible aryl ketones such as benzophenone and acetophenone are of particular importance inasmuch as these groups are subject to multiple reactivation in water and hence provide increased coating efficiency.

The azides constitute a preferred class of photoreactive species and include derivatives based on arylazides ($C_6R_5N_3$) such as phenyl azide and particularly 4-fluoro-3-nitrophenyl azide, acyl azides (—CO—$N_3$) such as benzoyl azide and p-methylbenzoyl azide, azido formates (—O—CO—$N_3$) such as ethyl azidoformate, phenyl azidoformate, sulfonyl azides (—$SO_2$—$N_3$) such as benzenesulfonyl azide, and phosphoryl azides $(RO)_2PON_3$ such as diphenyl phosphoryl azide and diethyl phosphoryl azide. Diazo compounds constitute another class of photoreactive species and include derivatives of diazoalkanes (—$CHN_2$) such as diazomethane and diphenyldiazomethane, diazoketones (—CO—$CHN_2$) such as diazoacetophenone and 1-trifluoromethyl-1-diazo-2-pentanone, diazoacetates (—O—CO—$CHN_2$) such as t-butyl diazoacetate and phenyl diazoacetate, and beta-keto-alpha-diazoacetates (—CO—$CN_2$—CO—O—) such as t-butyl alpha diazoacetoacetate. Other photoreactive species include the diazirines (—$CHN_2$) such as 3-trifluoromethyl-3-phenyldiazirine, and ketenes (—CH=C=O) such as ketene and diphenylketene.

Upon activation of the photoreactive species, the coating agents are covalently bound to each other and/or to the material surface by covalent bonds through residues of the photoreactive species. Exemplary photoreactive species, and their residues upon activation, are shown as follows.

| Photoreactive | Group | Residue Functionality |
|---|---|---|
| aryl azides | amine | R—NH—R' |
| acyl azides | amide | R—CO—NH—R' |
| azidoformates | carbamate | R—O—CO—NH—R' |
| sulfonyl azides | sulfonamide | R—$SO_2$—NH—R' |
| phosphoryl azides | phosphoramide | $(RO)_2$PO—NH—R' |
| diazoalkanes | new C—C bond | |
| diazoketones | new C—C bond and ketone | |
| diazoacetates | new C—C bond and ester | |
| beta-keto-alpha-diazoacetates | new C—C bond and beta-ketoester | |
| aliphatic azo | new C—C bond | |
| diazirines | new C—C bond | |
| ketenes | new C—C bond | |
| photoactivated ketones | new C—C bond and alcohol | |

The coating agents of the present invention can be applied to any surface having carbon-hydrogen bonds, with which the photoreactive species can react to immobilize the coating agents to surfaces. Examples of suitable surfaces are described in more detail below.

A composition of the present invention includes about 0 to about 93.9 mole %, preferably from about 30 to about 70 mole %, and most preferably from about 40 to about 60 mole % of a suitable hydrophilic monomer component. Suitable hydrophilic monomers provide an optimal combination of such properties as water solubility, biocompatability, and wettability. Most preferably, the hydrophilic monomer improves or provides the resultant polymeric complex with improved water solubility, though noting that the carboxylic acid-containing monomer may be hydrophilic as well, and can contribute to this effect.

Hydrophilic monomers are preferably taken from the group consisting of alkenyl substituted amides. Examples of preferred hydrophilic monomers include acrylamide, N-vinylpyrrolidone, methacrylamide, acrylamido propane-sulfonic acid (AMPS). Acrylamide is an example of a particularly preferred hydrophilic monomer.

Such monomers are available commercially from a variety of sources, e.g., Sigma-Aldrich, Inc. (St. Louis, Mo.) and Polysciences, Inc. (Warrington, Pa.).

The word "medicament", as used herein, will refer to a wide range of biologically active materials or drugs that can be incorporated into a coating composition of the present invention. The substances to be incorporated preferably do not chemically interact with the composition during fabrication, or during the release process.

Additives such as inorganic salts, BSA (bovine serum albumin), and inert organic compounds can be used to alter the profile of substance release, as known to those skilled in the art. The term "medicament", in turn, will refer to a peptide, protein, carbohydrate, nucleic acid, lipid, polysaccharide or combinations thereof, or synthetic inorganic or organic molecule, that causes a biological effect when administered in vivo to an animal, including but not limited to birds and mammals, including humans. Nonlimiting examples are antigens, enzymes, hormones, receptors, peptides, and gene therapy agents. Examples of suitable gene therapy agents include a) therapeutic nucleic acids, including antisense DNA and antisense RNA, and b) nucleic acids encoding therapeutic gene products, including plasmid DNA and viral fragments, along with associated promoters and excipients. Examples of other molecules that can be incorporated include nucleosides, nucleotides, antisense, vitamins, minerals, and steroids.

Coating compositions prepared according to this process can be used to deliver drugs such as nonsteroidal anti-inflammatory compounds, anesthetics, chemotherapeutic agents, immunotoxins, immunosuppressive agents, steroids, antibiotics, antivirals, antifungals, and steroidal antiinflammatories, anticoagulants. For example, hydrophobic drugs such as lidocaine or tetracaine can be included in the coating and are released over several hours.

Classes of medicaments which can be incorporated into coatings of this invention include, but are not limited to, anti-AIDS substances, anti-cancer substances, antibiotics, anti-viral substances, enzyme inhibitors, neurotoxins, opioids, hypnotics, antihistamines, immunosuppresents (e.g., cyclosporin), tranquilizers, anti-convulsants, muscle relaxants and anti-Parkinson substances, anti-spasmodics and muscle contractants, miotics and anti-cholinergics, immunosuppressants (e.g. cyclosporine) anti-glaucoma solutes, anti-parasite and/or anti-protozoal solutes, anti-hypertensives, analgesics, anti-pyretics and anti-inflammatory agents (such as NSAID's), local anesthetics, ophthalmics, prostaglandins, anti-depressants, anti-psychotic substances, anti-emetics, imaging agents, specific targeting agents, neurotransmitters, proteins and cell response modifiers. A more complete listing of classes of medicaments may be found in the Pharmazeutische Wirkstoffe, ed. A. Von Kleemann and J. Engel, Georg Thieme Verlag, Stuttgart/New York, 1987, incorporated herein by reference.

Antibiotics are art recognized and are substances which inhibit the growth of or kill microorganisms. Antibiotics can be produced synthetically or by microorganisms. Examples of antibiotics include penicillin, tetracycline, chloramphenicol, minocycline, doxycycline, vancomycin, bacitracin, kanamycin, neomycin, gentamycin, erythromycin and cephalosporins. Examples of cephalosporins include cephalothin, cephapirin, cefazolin, cephalexin, cephradine, cefadroxil, cefamandole, cefoxitin, cefaclor, cefuroxime, cefonicid, ceforanide, cefotaxime, moxalactam, ceftizoxime, ceftriaxone, and cefoperazone.

Antiseptics are recognized as substances that prevent or arrest the growth or action of microorganisms, generally in a nonspecific fashion, e.g., either by inhibiting their activity or destroying them. Examples of antiseptics include silver sulfadiazine, chlorhexidine, glutaraldehyde, peracetic acid, sodium hypochlorite, phenols, phenolic compounds, iodophor compounds, quaternary ammonium compounds, and chlorine compounds.

Anti-viral agents are substances capable of destroying or suppressing the replication of viruses. Examples of anti-viral agents include α-methyl-P-adamantane methylamine), hydroxyethoxymethylguanine, adamantanamine, 5-iodo-2'-deoxyuridine, trifluorothymidine, interferon, and adenine arabinoside.

Enzyme inhibitors are substances which inhibit an enzymatic reaction. Examples of enzyme inhibitors include edrophonium chloride, N-methylphysostigmine, neostigmine bromide, physostigmine sulfate, tacrine HCL, tacrine, 1-hydroxy maleate, iodotubercidin, p-bromotetramisole, 10-(a-diethylaminopropionyl)-phenothiazine hydrochloride, calmidazolium chloride, hemicholinium-3,3,5-dinitrocatechol, diacylglycerol kinase inhibitor I, diacylglycerol kinase inhibitor II, 3-phenylpropargylaminie, N-monomethyl-L-arginine acetate, carbidopa, 3-hydroxybenzylhydrazine HCl, hydralazine HCl, clorgyline HCl, deprenyl HCl, L(−), deprenyl HCl, D(+), hydroxylamine HCl, iproniazid phosphate, 6-MeO-tetrahydro-9H-pyrido-indole, nialamide, pargyline HCl, quinacrine HCl, semicarbazide HCl, tranylcypromine HCl, N,N-diethylaminoethyl-2,2-diphenylvalerate hydrochloride, 3-isobutyl-1-methylxanthne, papaverine HCl, indomethacind, 2-cyclooctyl-2-hydroxyethylamine hydrochloride, 2,3-dichloro-a-methylbenzylamine (DCMB), 8,9-dichloro-2,3,4,5-tetrahydro-1H-2-benzazepine hydrochloride, p-aminoglutethimide, p-aminoglutethimide tartrate, R(+), p-aminoglutethimide tartrate, S(−), 3-iodotyrosine, alpha-methyltyrosine, L(−), alpha-methyltyrosine, D L(−), cetazolamide, dichlorphenamide, 6-hydroxy-2-benzothiazolesulfonamide, and allopurinol.

Anti-pyretics are substances capable of relieving or reducing fever. Anti-inflammatory agents are substances capable of counteracting or suppressing inflammation. Examples of such agents include aspirin (salicylic acid), indomethacin, sodium indomethacin trihydrate, salicylamide, naproxen, colchicine, fenoprofen, sulindac, diflunisal, diclofenac, indoprofen and sodium salicylamide. Local anesthetics are substances which have an anesthetic effect in a localized region. Examples of such anesthetics include procaine, lidocaine, tetracaine and dibucaine.

Imaging agents are agents capable of imaging a desired site, e.g., tumor, in vivo. Examples of imaging agents include substances having a label which is detectable in vivo, e.g., antibodies attached to fluorescent labels. The term antibody includes whole antibodies or fragments thereof.

Cell response modifiers are chemotactic factors such as platelet-derived growth factor (pDGF). Other chemotactic factors include neutrophil-activating protein, monocyte chemoattractant protein, macrophage-inflammatory protein, SIS (small inducible secreted), platelet factor, platelet basic protein, melanoma growth stimulating activity, epidermal growth factor, transforming growth factor (alpha), fibroblast growth factor, platelet-derived endothelial cell growth factor, insulin-like growth factor, nerve growth factor and bone growth/cartilage-inducing factor (alpha and beta). Other cell response modifiers are the interleukins, interleukin inhibitors or interleukin receptors, including interleukin 1 through interleukin 10; interferons, including alpha, beta and gamma; hematopoietic factors, including erythropoietin, granulocyte colony stimulating factor, macrophage colony stimulating factor and granulocyte-macrophage colony stimulating factor; tumor necrosis factors, including alpha and beta; transforming growth factors (beta), including beta-1, beta-2, beta-3, inhibin, activin, and DNA that encodes for the production of any of these proteins.

The coating composition of the present invention can be used in combination with a variety of devices, including those used on a temporary, transient or permanent basis upon and/or within the body.

Examples of medical devices suitable for the present invention include, but are not limited to catheters, implantable vascular access ports, blood storage bags, vascular stents, blood tubing, central venous catheters, arterial catheters, vascular grafts, intraaortic balloon pumps, heart valves, cardiovascular sutures, total artificial hearts and ventricular assist pumps, extracorporeal devices such as blood oxygenators, blood filters, hemodialysis units, hemoperfusion units, plasmapheresis units, hybrid artificial organs such as pancreas or liver and artificial lungs, as well as filters adapted for deployment in a blood vessel in order to trap emboli (also known as "distal protection devices").

Devices which are particularly suitable include vascular stents such as self-expanding stents and balloon expandable stents. Examples of self-expanding stents useful in the present invention are illustrated in U.S. Pat. Nos. 4,655,771 and 4,954,126 issued to Wallsten and 5,061,275 issued to Wallsten et al. Examples of appropriate balloon-expandable stents are shown in U.S. Pat. No. 4,733,665 issued to Palmaz, U.S. Pat. No. 4,800,882 issued to Gianturco and U.S. Pat. No. 4,886,062 issued to Wiktor. Similarly, urinary implants such as drainage catheters are also particularly appropriate for the invention.

The surfaces of the medical devices may be formed from polymeric, metallic and/or ceramic materials. Suitable polymeric materials include, without limitation, polyurethane and its copolymers, silicone and its copolymers, ethylene vinyl-acetate, thermoplastic elastomers, polyvinyl chloride, polyolefins, cellulosics, polyamides, polyesters, polysulfones, polytetrafluorethylenes, polycarbonates, acrylonitrile butadiene styrene copolymers, acrylics, polylactic acid, polyglycolic acid, polycaprolactone, polylactic acid-polyethylene oxide copolymers, cellulose, collagens, and chitins.

Metallic materials include metals and alloys based on titanium (such as nitinol, nickel titanium alloys, thermo-memory alloy materials), stainless steel, tantalum, nickel-chrome, or cobalt-chromium (such those available under the tradenames Elgiloy™ and Phynox™). Metallic materials also include clad composite filaments, such as those disclosed in WO 94/16646. Examples of ceramic materials include ceramics of alumina and glass-ceramics such as those available under the tradename Macor™.

The substrates that can be coated with a composition of the present invention include materials that are substantially insoluble in body fluids and that are generally designed and constructed to be placed in or onto the body or to contact fluid of the body. The substrates preferably have the physical properties such as strength, elasticity, permeability and flexibility required to function for the intended purpose; can be purified, fabricated and sterilized easily; will substantially maintain their physical properties and function during the time that they remain implanted in or in contact with the body. Examples of such substrates include: metals such as titanium/titanium alloys, TiNi (shape memory/super elastic), aluminum oxide, platinum/platinum alloys, stainless steels, MP35N, elgiloy, haynes 25, stellite, pyrolytic carbon, silver or glassy carbon; polymers such as polyurethanes, polycarbonates, silicone elastomers, polyolefins including polyethylenes or polypropylenes, polyvinyl chlorides, polyethers, polyesters, nylons, polyvinyl pyrrolidones, polyacrylates and polymethacrylates such as polymethylmethacrylate ("PMMA"), n-Butyl cyanoacrylate, polyvinyl alcohols, polyisoprenes, rubber, cellulosics, polyvinylidene fluoride ("PVDF"), polytetrafluoroethylene, ethylene tetrafluoroethylene copolymer ("ETFE"), acrylonitrile butadiene ethylene, polyamide, polyimide, styrene acrylonitrile, and the like; minerals or ceramics such as hydroxyapatite; human or animal protein or tissue such as bone, skin, teeth, collagen, laminin, elastin or fibrin; organic materials such as wood, cellulose, or compressed carbon; and other materials such as glass, or the like.

Substrates made using these materials can be coated or remain uncoated, and derivatized or remain underivatized. Medical devices upon or into which the composition can be coated include, but are not limited to, surgical implants, prostheses, and any artificial part or device which replaces or augments a part of a living body or comes into contact with bodily fluids, particularly blood. The substrates can be in any shape or form including tubular, sheet, rod and articles of proper shape. Various medical devices and equipment usable in accordance with the invention are known in the art. Examples of devices include catheters, suture material, tubing, and fiber membranes. Examples of catheters include central venous catheters, thoracic drain catheters, angioplasty balloon catheters. Examples of tubing include tubing used in extracorporeal circuitry, such as whole blood oxygenators. Examples of membranes include polycarbonate membranes, haemodialysis membranes, membranes used in diagnostic or biosensor devices. Also included are devices used in diagnosis, as well as polyester yarn suture material such as polyethylene ribbon, and polypropylene hollow fiber membranes.

Further illustrations of medical devices include the following: autotransfusion devices, blood filters, blood pumps, blood temperature monitors, bone growth stimulators, breathing circuit connectors, bulldog clamps, cannulae, grafts, implantible pumps, impotence and incontinence implants, intra-ocular lenses, leads, lead adapters, lead connectors, nasal buttons, orbital implants, cardiac insulation pads, cardiac jackets, clips, covers, dialators, dialyzers, disposable temperature probes, domes, drainage products, drapes, ear wicks, electrodes, embolic devices, esophageal stethoscopes, fracture fixation devices, gloves, guide wires, hemofiltration devices, hubs, intra-arterial blood gas sensors, intracardiac suction devices, intrauterine pressure devices, nasal spetal splints, nasal tampons, needles, ophthalmic devices, PAP brushes, periodontal fiber adhesives, pessary, retention cuffs, sheeting, staples, stomach ports, surgical instruments, transducer protectors, ureteral stents, vaginal contraceptives, valves, vessel loops, water and saline bubbles, acetabular cups, annuloplasty ring, aortic/coronary locators, artificial pancreas, batteries, bone cement, breast implants, cardiac materials, such as fabrics, felts, mesh, patches, cement spacers, cochlear implant, defibrillators, generators, orthopedic implants, pacemakers, patellar buttons, penile implant, pledgets, plugs, ports, prosthetic heart valves, sheeting, shunts, umbilical tape, valved conduits, and vascular access devices.

Generally, a solution of the copolymer is prepared at a concentration of about 1% to a concentration of about 10% in water or an aqueous buffer solution. Depending on the surface being coated, an organic solvent such as isopropyl alcohol ("IPA") can be included in the solution at concentrations varying from about 1 to about 40%. The medical device or surface to be coated can be dipped into the copolymer solution, or, alternatively, the copolymer solution can be applied to the surface of the device by spraying or the like. At this point, the device can be air-dried to evaporate the solvent or can proceed to the illumination step without drying. The devices can be rotated and illuminated with UV light for 5-10 minutes to insure an even coat of the coating. This process can be repeated multiple times to attain the desired coating thickness. Coating thicknesses can be evaluated using scanning electron microscopy (SEM) in both the dry and hydrated forms. The difference in thickness between the dry and the hydrated condition is not generally significant. The thickness of the coating ranges from about 0.5 microns to about 20 microns and preferably from about 2 microns to about 10 microns.

If a significant amount of surface area is to be coated, it may be preferable to place the device in a rotating fixture to facilitate the coverage of the device's surface. For example, to coat the entire surface of a vascular stent, the ends of the device are fastened to a rotating fixture by resilient retainers, such as alligator clips. The stent is rotated in a substantially horizontal plane around its axis. The spray nozzle of the airbrush is typically placed 2-4 inches from the device. The thickness of the coating can be adjusted by the speed of rotation and the flow rate of the spray nozzle.

Medicament is typically incorporated into the matrix after the matrix itself has been coated onto a medical device. Generally a solution of medicament or medicaments is prepared and the matrix-coated device is soaked in the solution. Medicament is absorbed into the matrix from the solution. Various solvents can be used to form the medicament solution as the amount of medicament absorbed by the matrix can be controlled by the solvent solution. Likewise, the pH and/or the ionic strength of the medicament solution can be adjusted to control the degree of medicament absorption by the matrix. After soaking in medicament solution for a period of time, the medical device is removed and air dried.

A coating of the present invention is preferably sufficiently durable and tenacious to permit the coating to remain on the device surface, in vivo, for a period of time sufficient for its intended use, including the delivery of medicaments. The durability and/or tenacity of various coatings, on various surfaces, can be assessed using conventional techniques.

Applicants, for instance, have constructed a device that includes the use of an adjustable O-ring connected to a high-end torque screw-driver. Using this device it is possible to place a constant and replicable force on a coated medical device, e.g., a catheter. The coated medical device to be tested is inserted into the O-ring and the torque applied to a desired level. The coated device is pulled through the device a predetermined number of times. The coated device is then removed from the O-ring and the device evaluated to determine the amount of matrix remaining on the surface. The matrix remaining on the surface can be detected either directly, e.g., by staining, and/or indirectly, e.g., using a drug loading and release assay. After 5 cycles through the device described above, a medical device coated with a formulation of the present invention, preferably retains the ability to absorb and release at least 75% of its initial capacity.

Other suitable biomaterials include those substances that do not possess abstractable hydrogens to which the photogroups can form covalent bonds. Such biomaterials can be used in a variety of ways. For instance, biomaterials can be made suitable for coating via photochemistry by applying a suitable primer coating which bonds to the biomaterial surface and provides a suitable substrate for binding by the photogroups. For instance, metals and ceramics having oxide groups on their surfaces can be made suitable for coupling via photochemistry by adding a primer coating that binds to the oxide groups and provides abstractable hydrogens. Such metals include, but are not limited to, titanium, stainless steel, and cobalt chromium, while such ceramics can include, but are not limited to, silicon nitride, silicon carbide, zirconia, and alumina, as well as glass, silica, and sapphire. One suitable class of primers for metals and ceramics are organosilane reagents, which bond to the oxide surface and provide hydrocarbon groups (Brzoska, J. B., et. al., *Langmuir* 10:4367-4373, 1994). This reference teaches that —SiH groups are suitable alternatives for bonding of photogroups.

Similarly, various tie layers can be applied to various metals, glass, and ceramics, which can in turn serve as sources of abstractable hydrogens for photochemical coupling to the surface. Various polymeric materials such as Nylon, polystyrene, polyurethane, polyethylene terepthalate, and various monomeric analogs used to prepare such polymers could be used for such tie layers. See, for instance, U.S. Pat. Nos. 5,443,455; 5,749,837; 5,769,796; 5,997,517.

The present invention further includes the optional use of additional, e.g., "clad", layers covering and/or between layers of the composition in either a continuous or discontinuous fashion. For instance, one or more outer layers of one or more other materials, e.g., a hydrophilic or protective outer coating, can be photoimmobilized or otherwise bound, absorbed or attached on or to a coating prepared as described herein.

If desired, for instance, such an additional coating can be applied on top of a medicament absorbing layer, either before and/or after medicament has been absorbed into the matrix. It is preferable to add the additional layer before medicament has been absorbed. For instance, a solution of the same or of a different copolymer can be prepared and the coated device dipped, sprayed or otherwise contacted with the solution and illuminated as described previously. The coated device can then be contacted with, e.g., soaked in, the medicament solution as described previously. Medicament will pass through the top coat and be absorbed by the underlying matrix. When placed in the body, the medicament will be released as described herein. Using such a method, a coating with enhanced lubricity, hemocompatibility, or other desired property can be incorporated into the medical device surface, thus forming a device coating that provides multiple desired properties.

The invention will be further described with reference to the following non-limiting examples.

EXAMPLES

Example 1

Preparation of 4-Benzoylbenzoyl Chloride (BBA-Cl) (Compound I)

4-Benzoylbenzoic acid (BBA), 1.0 kg (4.42 moles), was added to a dry 5 liter Morton flask equipped with reflux condenser and overhead stirrer, followed by the addition of 645 ml (8.84 moles) of thionyl chloride and 725 ml of toluene. Dimethylformamide, 3.5 ml, was then added and the mixture was heated at reflux for 4 hours. After cooling, the solvents were removed under reduced pressure and the residual thionyl chloride was removed by three evaporations using 3×500 ml of toluene. The product was recrystallized from 1:4 toluene:hexane to give 988 g (91% yield) after drying in a vacuum oven. Product melting point was 92-94° C. Nuclear magnetic resonance ("NMR") analysis at 80 MHz ($^1$H NMR (CDCl$_3$)) was consistent with the desired product: aromatic protons 7.20-8.25 (m, 9H). All chemical shift values are in ppm downfield from a tetramethylsilane internal standard. The final compound (Compound I shown below) was stored for use in the preparation of a monomer used in the synthesis of photoactivatable polymers as described, for instance, in Example 3.

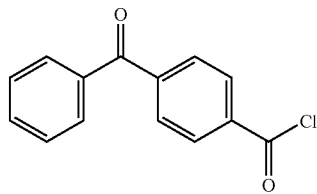

Compound I

Example 2

Preparation of N-(3-Aminopropyl)methacrylamide Hydrochloride (APMA) (Compound II)

A solution of 1,3-diaminopropane, 1910 g (25.77 moles), in 1000 ml of CH$_2$Cl$_2$ was added to a 12 liter Morton flask and cooled on an ice bath. A solution of t-butyl phenyl carbonate, 1000 g (5.15 moles), in 250 ml of CH$_2$Cl$_2$ was then added dropwise at a rate which kept the reaction temperature below 15° C. Following the addition, the mixture was warmed to room temperature and stirred 2 hours. The reaction mixture was diluted with 900 ml of CH$_2$Cl$_2$ and 500 g of ice, followed by the slow addition of 2500 ml of 2.2 N NaOH. After testing to insure the solution was basic, the product was transferred to a separatory funnel and the organic layer was removed and set aside as extract #1. The aqueous was then extracted with 3×1250 ml of CH$_2$Cl$_2$, keeping each extraction as a separate fraction. The four organic extracts were then washed successively with a single 1250 ml portion of 0.6 N NaOH beginning with fraction #1 and proceeding through fraction #4. This wash procedure was repeated a second time with a fresh 1250 ml portion of 0.6 N NaOH. The organic extracts were then combined and dried over Na$_2$SO$_4$. Filtration and evaporation of solvent to a constant weight gave 825 g of N-mono-t-BOC-1,3-diaminopropane which was used without further purification.

A solution of methacrylic anhydride, 806 g (5.23 moles), in 1020 ml of CHCl$_3$ was placed in a 12 liter Morton flask equipped with overhead stirrer and cooled on an ice bath. Phenothiazine, 60 mg, was added as an inhibitor, followed by the dropwise addition of N-mono-t-BOC-1,3-diaminopropane, 825 g (4.73 moles), in 825 ml of CHCl$_3$. The rate of addition was controlled to keep the reaction temperature below 10° C. at all times. After the addition was complete, the ice bath was removed and the mixture was left to stir overnight. The product was diluted with 2400 ml of water and transferred to a separatory funnel. After thorough mixing, the aqueous layer was removed and the organic layer was washed with 2400 ml of 2 N NaOH, insuring that the aqueous layer was basic. The organic layer was then dried over Na$_2$SO$_4$ and filtered to remove drying agent. A portion of the CHCl$_3$ solvent was removed under reduced pressure until the combined weight of the product and solvent was approximately 3000 g. The desired product was then precipitated by slow addition of 11.0 liters of hexane to the stirred CHCl$_3$ solution, followed by overnight storage at 4° C. The product was isolated by filtration and the solid was rinsed twice with a solvent combination of 900 ml of hexane and 150 ml of CHCl$_3$. Thorough drying of the solid gave 900 g of N-[N'-(t-butyloxycarbonyl)-3-aminopropyl]-methacrylamide, m.p. 85.8° C. by differential scanning calorimetry ("DSC"). Analysis on an NMR spectrometer was consistent with the desired product: $^1$H NMR (CDCl$_3$) amide NH's 6.30-6.80, 4.55-5.10 (m, 2H), vinyl protons 5.65, 5.20 (m, 2H), methylenes adjacent to N 2.90-3.45 (m, 4H), methyl 1.95 (m, 3H), remaining methylene 1.50-1.90 (m, 2H), and t-butyl 1.40 (s, 9H).

A 3-neck, 2 liter round bottom flask was equipped with an overhead stirrer and gas sparge tube. Methanol, 700 ml, was added to the flask and cooled on an ice bath. While stirring, HCl gas was bubbled into the solvent at a rate of approximately 5 liters/minute for a total of 40 minutes. The molarity of the final HCl/MeOH solution was determined to be 8.5 M by titration with 1 N NaOH using phenolphthalein as an indicator. The N-[N'-(t-butyloxycarbonyl)-3-aminopropyl] methacrylamide, 900 g (3.71 moles), was added to a 5 liter Morton flask equipped with an overhead stirrer and gas outlet adapter, followed by the addition of 1150 ml of methanol solvent. Some solids remained in the flask with this solvent volume. Phenothiazine, 30 mg, was added as an inhibitor, followed by the addition of 655 ml (5.57 moles) of the 8.5 M HCl/MeOH solution. The solids slowly dissolved with the evolution of gas but the reaction was not exothermic. The mixture was stirred overnight at room temperature to insure complete reaction. Any solids were then removed by filtration and an additional 30 mg of phenothiazine were added. The solvent was then stripped under reduced pressure and the resulting solid residue was azeotroped with 3×1000 ml of isopropanol with evaporation under reduced pressure. Finally, the product was dissolved in 2000 ml of refluxing isopropanol and 4000 ml of ethyl acetate were added slowly with stirring. The mixture was allowed to cool slowly and was stored at 4° C. overnight. Compound II was isolated by filtration and was dried to constant weight, giving a yield of 630 g with a melting point of 124.7° C. by DSC. Analysis on an NMR spectrometer was consistent with the desired product: $^1$H NMR ($D_2O$) vinyl protons 5.60, 5.30 (m, 2H), methylene adjacent to amide N 3.30 (t, 2H), methylene adjacent to amine N 2.95 (t, 2H), methyl 1.90 (m, 3H), and remaining methylene 1.65-2.10 (m, 2H). The final compound (Compound II shown below) was stored for use in the preparation of a monomer used in the synthesis of photoactivatable polymers as described, for instance, in Example 3.

Compound II

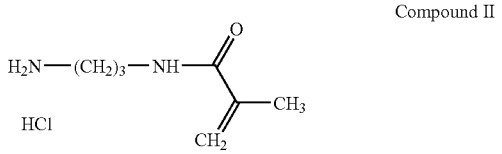

Example 3

Preparation of N-[3-(4-Benzoylbenzamido)propyl]methacrylamide (BBA-APMA) (Compound III)

Compound II 120 g (0.672 moles), prepared according to the general method described in Example 2, was added to a dry 2 liter, three-neck round bottom flask equipped with an overhead stirrer. Phenothiazine, 23-25 mg, was added as an inhibitor, followed by 800 ml of chloroform. The suspension was cooled below 10° C. on an ice bath and 172.5 g (0.705 moles) of Compound I, prepared according to the general method described in Example 1, were added as a solid. Triethylamine, 207 ml (1.485 moles), in 50 ml of chloroform was then added dropwise over a 1-1.5 hour time period. The ice bath was removed and stirring at ambient temperature was continued for 2.5 hours. The product was then washed with 600 ml of 0.3 N HCl and 2×300 ml of 0.07 N HCl. After drying over sodium sulfate, the chloroform was removed under reduced pressure and the product was recrystallized twice from 4:1 toluene:chloroform using 23-25 mg of phenothiazine in each recrystallization to prevent polymerization. Typical yields of Compound III were 90% with a melting point of 147-151° C. Analysis on an NMR spectrometer was consistent with the desired product: $^1$H NMR ($CDCl_3$) aromatic protons 7.20-7.95 (m, 9H), amide NH 6.55 (broad t, 1H), vinyl protons 5.65, 5.25 (m, 2H), methylenes adjacent to amide N's 3.20-3.60 (m, 4H), methyl 1.95 (s, 3H), and remaining methylene 1.50-2.00 (m, 2H). The final compound (Compound III shown below) was stored for use in the synthesis of photoactivatable polymers as described in Examples 4 and 5.

Compound III

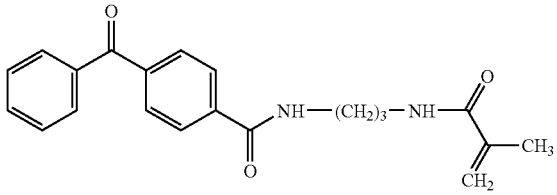

Example 4

Preparation of Polyacrylamide(36%)co-Methacrylic acid(MA)-(10%)co-Methoxy PEG1000MA-(4%)co-BBA-APMA (Compound IV)

Acrylamide, 39.3 g (0.55 mole), and BBA-APMA (Compound III), 15.5 g (0.04 mole), were dissolved in dimethylsulfoxide ("DMSO"), followed by methoxypolyethyleneglycol 1000 monomethacrylate (methoxy PEG 1000 MA), 110.8 g (0.11 mole), methacrylic acid, 33.8 ml (0.4 mole), 2,2'-azobisisobutyronitrile ("AIBN"), 2.3 g (0.01 mole), and N,N, N',N',-tetramethylethylenediamine ("TEMED"), 2.2 ml (0.02 mole). The solution was deoxygenated with a helium sparge for 60 minutes at 60° C., then sealed under argon and heated overnight at 60° C. The resulting product was dialyzed against deionized water using 12,000-14,000 molecular weight cutoff tubing for 66 to 96 hours, then filtered through Whatman #1 filter paper before being lyophilized to give 190 g of polymer. The resultant polymer was identified as methacrylic acid-co-methoxy PEG1000-MA-co-BBA-APMA having the following general structure (Compound IV).

Compound IV

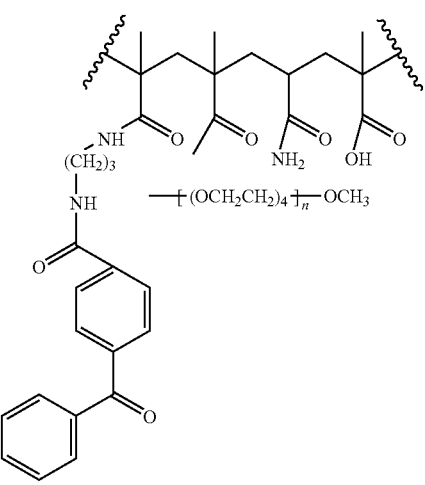

Example 5

Preparation of Various Analogs of Compound (IV)

A series of polymers of the general formula of Compound IV were synthesized as generally described in Example 4. The mole percent of acrylamide and methoxy PEG1000 monomethacrylate were varied while the mole percent of the BBA-APMA (Compound III) was constant at four mole percent. The ratios of the other groups to carbonyl groups in the various polymers were calculated assuming each mole of the methoxy PEG1000 monomethacrylate contained 23 ether groups. A list of the various polymers prepared and the composition of the various polymers are listed below.

The following compounds were synthesized in a manner analogous to that described above with respect to Compound IV.

2. 4% BBA-APMA, 10% methoxy PEG1000 monomethacrylate, 86% Methacrylic acid (Polymer #8 in table below)
3. 4% BBA-APMA, 2% methoxy PEG1000 monomethacrylate, 66% Acrylamide, 28% Methacrylic acid (Polymer #1 in table below)
4. 4% BBA-APMA, 2% methoxy PEG1000 monomethacrylate, 42% Acrylamide, 52% Methacrylic acid (Polymer #2 in table below)
5. 4% BBA-APMA, 26% methoxy PEG1000 monomethacrylate, 42% Acrylamide, 28% Methacrylic acid (Polymer #3 in table below)
6. 4% BBA-APMA, 2% methoxy PEG1000 monomethacrylate, 54% Acrylamide, 40% Methacrylic acid (Polymer #4 in table below)
7. 4% BBA-APMA, 14% methoxy PEG1000 monomethacrylate, 54% Acrylamide, 28% Methacrylic acid (Polymer #5 in table below)
8. 4% BBA-APMA, 14% methoxy PEG1000 monomethacrylate, 42% Acrylamide, 40% Methacrylic acid (Polymer #6 in table below)
9. 4% BBA-APMA, 2% methoxy PEG1000 monomethacrylate, 42% Acrylamide, 52% Methacrylic acid
10. 4% BBA-APMA, 60% Acrylamide, 36% Methacrylic acid
11. 4% BBA-APMA, 50% Acrylamide, 46% Methacrylic acid
12. 4% BBA-APMA, 40% Acrylamide, 56% Methacrylic acid The mole % BBA-APMA was constant at 4 mole %. The ratios of ether groups to carboxyl groups in the various polymers were calculated assuming each mole of methoxy PEG1000 monomethacrylate contained 100/44=23 ether groups. The composition of the various polymers were:

| Polymer # | Mole % Acrylamide | Mole % MeO-PEG | Mole % Methacrylic Acid | Ratio O/COOH |
|---|---|---|---|---|
| 1 | 66 | 2 | 28 | 1.64 |
| 2 | 42 | 2 | 52 | 0.88 |
| 3 | 42 | 26 | 28 | 21.4** |
| 4 | 54 | 2 | 40 | 1.15 |
| 5 | 54 | 14 | 28 | 11.5** |
| 6 | 42 | 14 | 40 | 8.05** |
| 7 (Compound IV) | 50 | 10 | 36 | 6.39 |
| 8 | 86 | 10 | 0 | Undefined |

**Polymers #3, #5, and #6 were poorly soluble in water and difficult to coat.

Example 6

Release of Chlorhexidine Diacetate and Hexachlorophene on Stainless Steel Rods Tested against *Staphylococcus epidermidis*

Stainless steel (SS, 304) rods (0.75 in., 2 cm) were initially pretreated with Parylene C as follows: First, the rods were cleaned with Enprep 160SE detergent (Ethone-OMI Inc., Bridgeview, Ill.) followed by silylation with γ-methacryoxypropyltrimethoxysilane (Sigma Chemical Co., St. Louis, Mo.). Five grams of Parylene C (Specialty Coating Systems, Indianapolis, Ind.) was loaded into the vaporizer of a Labcoter 1, Parylene Deposition Unit, Model PDS 2010 (Specialty Coating Systems, Indianapolis, Ind.) and the parylene was deposited onto the rods in order to achieve a uniform and durable coating of the desired thickness. After precoating, the rods were wiped clean with a cloth soaked in isopropyl alcohol (IPA). A solution of Compound IV was prepared at a concentration of 50 mg/ml in 20% IPA. The rods were dipped at 1.0 cm (0.4 in.)/sec into and 0.5 cm (0.2 in.)/sec out of solution (with no dwell period for the first application and a 30 sec dwell period for the second application). After air-drying for approximately 20 minutes, the coated rods were suspended midway between opposed ELC 4000 lamps (40 cm (15.7 in) apart) containing 400 watt mercury vapor bulbs which put out 1.5 mW/sq. cm from 330-340 nm at the point of illumination. The rods were rotated and illuminated for five minutes to insure an even coat of the coating. Two coats were applied.

Two separate solutions of chlorhexidine and hexachlorophene were prepared. Chlorhexidine diacetate ("CDA") (100 mg/ml) was dissolved in 70% ethanol (EtOH) and hexachlorophene ("HCP") was also dissolved in 70% EtOH by heating. The SS rods coated with Compound IV were incubated with either the CHA or HCP solution for 30 minutes at room temperature. The parts were air-dried overnight.

The longevity of the antiseptic release was evaluated by transferring the rods from one agar surface to a fresh agar surface for zone of inhibition analysis. Basically, the 2 cm (0.8 in.) SS rods were laid parallel on to a Mueller-Hinton agar surface that was incubated with approximately a $1 \times 10^6$ CFU/ml of *Staphylococcus epidermidis* (ATCC 35984). The agar plates containing the parts were incubated overnight at 37° C. The zones of inhibition or areas of no bacterial growth were measured across the diameter of the part. Samples were transferred daily to new agar plates with fresh lawns of *S. epidermidis* until no zones of inhibition were present.

The CDA containing rods produced zones starting at approximately 34 mm and leveling off to 15-18 mm by day 4 and continued at that size through day 14 while the HCP containing parts produced zones starting at approximately 33 mm and leveling off to 30 mm by day 3 and continued at that size through day 14 (end of experiment).

Example 7

Release of Chlorhexidine Digluconate ("CHG") on Stainless Steel Rods Tested against *Staphylococcus epidermidis, Staphylococcus aureus, Escherichia coli,* and *Candida albicans*

Stainless steel (SS, 304) rods (0.75 in., 2 cm) were pretreated and a solution of compound IV was prepared as described in Example 6. A portion of the rods (0.6 in., 1.6 cm) was dip-coated into the coating solution by dipping into the solution at 0.5 cm (0.2 in.)/sec, swelling for 30 seconds and withdrawing at a rate of 0.2 cm (0.08 in.)/sec for the first 1.2 cm (0.5 in.) of the rod, the reduced to 0.05 cm (0.02 in.) for the last 0.4 cm (0.16 in.) of the rod. The rods were air-dried for 15 minutes and UV illuminated for 5 minutes with rotation as described in Example 6. Two coats were applied.

Chlorhexidine digluconate (CHG) (100 mg/ml) was diluted further in deionized (DI) water. Compound IV-coated parylene treated and uncoated rods were sterilized for 20 minutes in 70% IPA and air-dried. All of the rods were soaked for one hour at room temperature in the CHG solution. The parts were then air-dried overnight.

The CHG-incorporated parts as well as uncoated and Compound-IV coated without CHG were tested in the zone of inhibition assay agent S. epidermidis (ATCC 35984), S. aureus (ATCC 25923) E. coli (ATCC 25922) and C. albicans (ATCC 10231) as described in Example 6.

The following results were obtained. S. epidermidis: The controls for both the uncoated and Compound IV-coated did not produce zones. The uncoated parts with CHG produced zones starting at 22 mm on day 1 and dropped off to no zones by day 4. The parylene-only coated samples with drug gave zones starting at 25 mm and dropped off to zero zones by day 5. The Compound IV-coated samples with CHG incorporated had zones starting at 25 mm, which leveled off to 15-20 mm by day 2 through day 14, and decreasing to 5 mm by day 21. E. coli: The controls with no drug for both uncoated and Compound IV-coated did not produce zones. The uncoated parts with CHG produced zones starting at 15 mm and dropped off with no zones by 4 days. The parylene-only sample with drug gave zones starting at 22 mm and dropped off to no zones by 5 days. The Compound IV-coated samples with drug had zones starting at 20 mm and gradually decreased to no zones by day 21. C. albicans: The controls with no drug for both uncoated and Compound IV-coated produced no zones. The uncoated parts with CHG produced zones starting at 17 mm for day one only. The parylene-only samples with drug gave zones starting at 19 mm and lasted only 2 days. The Compound IV-coated samples with drug gave zones that started at 28 mm and gradually decreased to zero zones by day 18. S. aureus: The controls with no drug for both uncoated and Compound IV-coated did not produce zones. The uncoated parts with CHG produced zones starting at 23 and dropped off to no zones by day 4. The parylene-only samples with drug gave zones starting at 25 mm and dropped off to no zones by day 3. The Compound IV-coated samples with drug had zones starting at 23 mm and gradually decreased to 13 mm through day 12. On day 13 the study was discontinued due to contamination.

Example 8

Release of Chlorhexidine Digluconate (CHG) on Titanium Rods Tested against S. epidermidis, S. aureus, E. coli, and C. albicans Titanium (90 Ti/6 Al/4V) rods (0.75 in., 2 cm) were pretreated with parylene and a Compound IV solution was prepared as described in Example 6. The rods were dip coated as described in Example 7, except that the entire rod was coated. The rods were air-dried and UV cured as described in Example 6. Two coats were applied.

The uncoated, parylene treated, and Compound IV-coated rods were sterilized in 70% IPA for 20 minutes and air-dried. The samples were then incorporated with CHG at 100 mg/ml in DI water for one hour at room temperature with agitation. The rods were rinsed by dipping three times into tubes containing DI water and air-dried overnight.

The quantity of CHG eluted from the rods was also determined. The individual rods were placed into test tubes containing 2 ml of Phosphate Buffer Saline ("PBS") and were incubated at 37° C. overnight with agitation. The rods were transferred to fresh PBS daily, and the eluates were diluted into the High Pressure Liquid Chromatography (HPLC) mobile phase to solubilize the CHG. The amount of CHG eluted was measured by HPLC and was determined to be 12.3 µg/rod for uncoated, 10.1 µg/rod for parylene-only, and 275 µg/rod for Compound IV-coated.

Also the CHG incorporated parts, as well as uncoated and Compound IV-coated without CHG were tested in the zone of inhibition assay against S. epidermidis (ATCC 35984), S. aureus (ATCC 25923) E. coli (ATCC 25922) and C. albicans (ATCC 10231) as described in Example 6. The results were as follows: S. epidermidis: The uncoated and parylene-only gave zone of 15-18 mm on day 1 and died off by day 3. The Compound IV-coated rods with drug gave zones starting at 24 mm, leveling at 15-19 mm from day 2-21 and then gradually decreasing to no zone on day 27. S. aureus: The uncoated and parylene-only gave zone of 14-16 mm on day 1 and dropped off to no zones by day 3. The Compound IV samples with drug gave zones starting at 20 mm and gradually decreasing to 12 mm on day 16. They were discontinued on day 20 due to contamination. E. coli: Uncoated and parylene-only gave zones of 13-14 mm on day 1 and dropped off to no zones by day 3. The Compound IV sample with drug gave zones starting at 20 mm and gradually decreased to no zones on day 20. C. albicans: Uncoated and parylene-only gave zone of 7-10 mm on day 1 and dropped off to no zone by day 2. The Compound IV samples with drug had zones starting at 19 mm and gradually decreased to no zones on day 21.

Example 9

Release of Benzalkonuim Chloride ("BAK") and CHG from Pebax™ Rods Tested against S. epidermidis and E. coli Pebax™ rods (0.75 in., 2 cm) were wiped clean with an IPA soaked cloth and a Compound IV solution was prepared as described in Example 6. The rods were dipped at 3.0 cm (1.2 in.)/sec into, 30 sec dwell, and a 3.0 cm (1.2 in.)/sec out of solution. The rods were air-dried for approximately ten minutes and UV illuminated for 3 minutes with rotation as described in Example 6. Two coats were applied and a portion of the Pebax™ rods were cut into 1 cm (0.4 in.) pieces for the zone of inhibition testing.

BAK and CHG were prepared at 100 mg/ml in DI water and the samples were incorporated for one hour at room temperature with agitation. The rods were rinsed three times in DI water and air-dried overnight.

The samples were tested in the zone of inhibition assay against S. epidermidis (ATCC 35984) and E. coli (ATCC 25922) as described in Example 6 except the rods were placed perpendicular into the agar. S. epidermidis results: The Compound IV coatings containing BAK gave zones starting at 26 mm and gradually decreasing to no zones by day 16. The CHG coated rods gave zones that started at 22 mm and gradually decreased to 12 mm on day 16 when the study was discontinued. E. coli: The BAK coated rods gave zones that started at 11 mm but lasted only 2 days. The CHG coated rods gave zones that started at 15 mm and gradually decreased to 9 mm on day 16 when the study was discontinued.

Example 10

Release of CHG form Polyurethane (Pellethane) Catheter Material Tested against *S. epidermidis*

The polyurethane (PU) catheter material was wiped clean with IPA and a solution of Compound IV for coating was prepared as described in Example 6. The rods were dip coated in the coating solution by dipping into the solution at 1.0 cm (0.4 in.)/sec, dwelling for 30 seconds, and withdrawing at a rate of 0.5 cm (0.2 in.)/sec. The rods were air-dried for 15 minutes and UV illuminated for three minutes with rotation as described in Example 6. Two coats of the Compound IV coating were applied.

The Compound IV coated rods were wiped with 70% IPA and dried for one hour. The rods were cut into 2 cm lengths and the CHG was incorporated by dipping the rods into a 200 mg/ml solution of CHG for one hour at room temperature and then rinsed three times in DI water. The samples were air-dried overnight and tested in the zone of inhibition assay against *S. epidermidis* (ATCC25984) as described in Example 6.

All of the uncoated samples and coated samples containing no drug produced no zones of inhibition. The Compound IV-coated zones with drug started at 28 mm at day zero and gradually decreased to no zones on day 23.

Example 11

Release of Alexidine Dihydrochloride ("ADC") from Polyurethane Rods Tested against *S. epidermidis*

Polyurethane rods (6 in., 15 cm) were wiped clean as described in Example 9 and a Compound IV solution was prepared as in Example 6. The rods were dip-coated by dipping into the solution at a rate of 2.0 cm (0.8 in.)/sec, dwelling for 30 seconds and withdrawing at 3.0 (1.2 in.)/sec. The samples were air-dried for 10 minutes and UV illuminated for two minutes with rotation as described in Example 6. Two coats were applied.

A solution of alexidine dihydrochloride (ADC) (100 mg/ml) in 50% methanol was prepared with heat. The PU rods were cut into 1 cm lengths and incorporated with the alexidine in the ADC solution in a warm water bath. The rods were incorporated for one hour, rinsed three times in DI water, and air-dried over night. The samples were tested in the zone of inhibition against *S. epidermidis* (ATCC 35984) as described in Example 6.

All of the uncoated samples and coated samples containing no drug produced no zones of inhibition. The Compound IV-coated zones with alexidine started at 12 mm and leveled off at 6-9 mm form day 2 through the duration of the test period of 21 days.

Example 12

Release of Vancomycin ("VA") on Coated PU Rods Tested against *S. epidermidis*

Polyurethane rods (6 in., 15 cm) were wiped clean as described in Example 9 and a Compound IV solution was prepared as in Example 6. The rods were dip coated in the coating solution by dipping into the solution at 2.0 cm (0.8 in.)/sec, dwelling for 30 seconds, and withdrawing at 2.0 (0.8 in.)/sec. The rods were air-dried for 15 minutes and UV illuminated for four minutes with rotation as described in Example 6. Two coats were applied.

A solution of vancomycin (VA) was prepared at 50 mg/ml in DI water. The rods were incorporated with VA in the VA solution for one hour at room temperature, rinsed three times in DI water, air-dried, and cut into 1 cm pieces. The samples were tested against *S. epidermidis* (ATCC35984) as described in Example 6.

All of the uncoated samples and coated samples containing no drug produced no zones of inhibition. The Compound IV coated zones with VA started at 20 mm and dropped off to no zones by day 6.

What is claimed is:

1. A coating composition for use in delivering a medicament from the surface of a medical device positioned in vivo, the composition comprising a polymeric reagent formed by the polymerization of the following monomers:
   a) about 1 to about 20 mole % of a polyether monomer,
   b) about 5 to about 75 mole % of a carboxylic acid-containing monomer, such that the effective ratio of ether groups to carboxylic acid groups in the resultant copolymer is between about 1 to 1 and about 10 to 1, and
   c) an amount of a hydrophilic monomer suitable to bring the composition to 100%.

2. A composition according to claim 1 wherein the polyether monomer comprises an alkoxy (poly)alkyleneglycol (meth)acrylate.

3. A composition according to claim 2 wherein the alkoxy group is selected from the group consisting of methoxy, ethoxy, propoxy, and butoxy.

4. A composition according to claim 2 wherein the (poly) alkylene glycol component of the alkoxy (poly)alkyleneglycol (meth)acrylate is selected from the group consisting of (poly)propylene glycol and (poly)ethylene glycol.

5. A composition according to claim 4 wherein the (poly) alkylene glycol has a nominal weight average molecular weight ranging from about 200 g/mole to about 2000 g/mole.

6. A composition according to claim 5 wherein the polyether monomer is selected from the group consisting essentially of methoxy (poly)ethylene glycol methacrylates, (poly) ethylene glycol methacrylates, and (poly)propylene glycol methacrylates.

7. A composition according to claim 1 wherein the polyether monomer is present in an amount of between about 5 and about 15 mole %.

8. A composition according to claim 1 wherein the carboxylic acid-containing monomer is selected from carboxyl substituted ethylene compounds.

9. A composition according to claim 8 wherein the carboxyl acid-containing monomer is selected from acrylic, methacrylic, maleic, crotonic, itaconic, and citraconic acid.

10. A composition according to claim 8 wherein the concentration of the carboxylic acid-containing monomer is between about 30 to about 50 mole %.

11. A composition according to claim 10 wherein the carboxylic-acid containing monomer comprises (meth)acrylic acid.

12. A composition according to claim 9 wherein the concentration of the carboxylic acid-containing monomer is between about 30 to about 50 mole % and the carboxylic acid containing monomer comprises (meth)acrylic acid.

13. A composition according to claim 1 wherein the photoderivatized monomer is selected from the group consisting of N-[3-(4-benzoylbenzoamido)propyl]methacrylamide, 9-vinyl anthracene, and 9-anthracenylmethyl methacrylate.

14. A composition according to claim 13 wherein the photoderivatized monomer is present in an amount of between about 1 to about 7 mole %.

15. A composition according to claim 1 wherein the hydrophilic monomer comprises an alkenyl substituted amide.

16. A composition according to claim 15 wherein the hydrophilic monomer is selected from the group consisting of acrylamide, N-vinylpyrrolidone, methacrylamide, and acrylamido propanesulfonic acid (AMPS).

17. A composition according to claim 16 wherein the hydrophilic monomer is present in an amount of between about 30 and about 70 mole %.

18. A composition according to claim 1 wherein the medicament is selected from the group consisting of peptides, proteins, carbohydrates, nucleic acids, lipids, polysaccharides and combinations thereof.

19. A composition according to claim 1 wherein the medicament is selected from the group consisting of gene therapy agents selected from therapeutic nucleic acids and nucleic acids encoding therapeutic gene products, antibiotics selected from penicillin, tetracycline, chloramphenicol, minocycline, doxycycline, vancomycin, bacitracin, kanamycin, neomycin, gentamycin, erythromycin and cephalosporins and antiseptics selected from silver sulfadiazine, chlorhexidine, glutaraldehyde, peracetic acid, sodium hypochlorite, phenols, phenolic compounds, iodophor compounds, quaternary ammonium compounds, and chlorine compounds.

20. A composition according to claim 1 wherein the device is selected from the group consisting of catheters, implantable vascular access ports, blood storage bags, vascular stents, blood tubing, central venous catheters, arterial catheters, vascular grafts, intraaortic balloon pumps, heart valves, cardiovascular sutures, total artificial hearts and ventricular assist pumps, extracorporeal devices such as blood oxygenators, blood filters, hemodialysis units, hemoperfusion units, plasmapheresis units, hybrid artificial organs such as pancreas or liver and artificial lungs and filters adapted for deployment in a blood vessel in order to trap emboli.

21. A crosslinked coating composition for use in delivering a medicament from the surface of a medical device positioned in vivo, the composition comprising a polymeric reagent in the form of a gel matrix, the polymeric reagent being formed by the polymerization of the following monomers:

a) about 1 to about 20 mole % of a polyether monomer, b) about 5 to about 75 mole % of a carboxylic acid-containing monomer, such that the effective ratio of ether groups to carboxylic acid groups in the resultant copolymer is between about 1 to 1 and about 10 to 1, c) about 0.1 to about 10 mole % of the residue of a photoderivatized monomer, and d) an amount of a hydrophilic monomer suitable to bring the composition to 100%.

22. A crosslinked composition according to claim 21 wherein the polyether monomer comprises an alkoxy (poly)alkyleneglycol (meth)acrylate.

23. A crosslinked composition according to claim 22 wherein the alkoxy group is selected from the group consisting of methoxy, ethoxy, propoxy, and butoxy.

24. A crosslinked composition according to claim 22 wherein the (poly)alkylene glycol component of the alkoxy (poly)alkyleneglycol (meth)acrylate is selected from the group consisting of (poly)propylene glycol and (poly)ethylene glycol.

25. A crosslinked composition according to claim 24 wherein the (poly)alkylene glycol component has a nominal weight average molecular weight ranging from about 200 g/mole to about 2000 g/mole.

26. A crosslinked composition according to claim 25 wherein the polyether monomer is selected from the group consisting essentially of methoxy (poly)ethylene glycol methacrylates, (poly)ethylene glycol methacrylates, and (poly)propylene glycol methacrylates.

27. A crosslinked composition according to claim 21 wherein the polyether monomer is present in an amount of between about 5 and about 15 mole %.

28. A crosslinked composition according to claim 21 wherein the carboxylic acid-containing monomer is selected from carboxyl substituted ethylene compounds.

29. A crosslinked composition according to claim 28 wherein the carboxyl acid-containing monomer is selected from acrylic, methacrylic, maleic, crotonic, itaconic, and citraconic acid.

30. A crosslinked composition according to claim 28 wherein the concentration of the carboxylic acid-containing monomer is between about 30 to about 50 mole %.

31. A crosslinked composition according to claim 30 wherein the carboxylic-acid containing monomer comprises (meth)acrylic acid.

32. A crosslinked composition according to claim 29 wherein the concentration of the carboxylic acid-containing monomer is between about 30 to about 50 mole % and the carboxylic acid containing monomer comprises (meth) acrylic acid.

33. A crosslinked composition according to claim 21 wherein the photoderivatized monomer is selected from the group consisting of N-[3-(4-benzoylbenzoamido)propyl] methacrylamide ("BBA-APMA"), 9-vinyl anthracene, and 9-anthracenylmethyl methacrylate.

34. A crosslinked composition according to claim 33 wherein the photoderivatized monomer is present in an amount of between about 1 to about 7 mole %.

35. A crosslinked composition according to claim 21 wherein the hydrophilic monomer comprises an alkenyl substituted amide.

36. A crosslinked composition according to claim 35 wherein the hydrophilic monomer is selected from the group consisting of acrylamide, N-vinylpyrrolidone, methacrylamide, and acrylamido propanesulfonic acid (AMPS).

37. A crosslinked composition according to claim 36 wherein the hydrophilic monomer is present in an amount of between about 30 and about 70 mole %.

38. A crosslinked composition according to claim 21 wherein the medicament is selected from the group consisting of peptides, proteins, carbohydrates, nucleic acids, lipids, polysaccharides and combinations thereof.

39. A crosslinked composition according to claim 21 wherein the medicament is selected from the group consisting of gene therapy agents selected from therapeutic nucleic acids and nucleic acids encoding therapeutic gene products, antibiotics selected from penicillin, tetracycline, chloramphenicol, minocycline, doxycycline, vancomycin, bacitracin, kanamycin, neomycin, gentamycin, erythromycin and cephalosporins and antiseptics selected from silver sulfadiazine, chlorhexidine, glutaraldehyde, peracetic acid, sodium hypochlorite, phenols, phenolic compounds, iodophor compounds, quaternary ammonium compounds, and chlorine compounds.

40. A crosslinked composition according to claim 21 wherein the device is selected from the group consisting of catheters, implantable vascular access ports, blood storage bags, vascular stents, blood tubing, central venous catheters, arterial catheters, vascular grafts, intraaortic balloon pumps, heart valves, cardiovascular sutures, total artificial hearts and ventricular assist pumps, extracorporeal devices such as blood oxygenators, blood filters, hemodialysis units, hemoperfusion units, plasmapheresis units, hybrid artificial organs such as pancreas or liver and artificial lungs and filters adapted for deployment in a blood vessel in order to trap emboli.

41. A composition according to claim 1 wherein the polyether monomer comprises an alkoxy (poly)alkyleneglycol (meth)acrylate, the carboxylic acid-containing monomer is selected from carboxyl substituted ethylene compounds, the photoderivatized monomer is selected from the group consisting of N-[3-(4-benzoylbenzoamido)propyl]methacrylamide, 9-vinyl anthracene, and 9-anthracenylmethyl methacrylate, and the hydrophilic monomer is selected from the group consisting of acrylamide, N-vinylpyrrolidone, methacrylamide, and acrylamido propanesulfonic acid (AMPS).

42. A composition according to claim 41 wherein the medicament is selected from the group consisting of gene therapy agents selected from therapeutic nucleic acids and nucleic acids encoding therapeutic gene products, antibiotics selected from penicillin, tetracycline, chloramphenicol, minocycline, doxycycline, vancomycin, bacitracin, kanamycin, neomycin, gentamycin, erythromycin and cephalosporins and antiseptics selected from silver sulfadiazine, chlorhexidine, glutaraldehyde, peracetic acid, sodium hypochlorite, phenols, phenolic compounds, iodophor compounds, quaternary ammonium compounds, and chlorine compounds and the device is selected from the group consisting of catheters, implantable vascular access ports, blood storage bags, vascular stents, blood tubing, central venous catheters, arterial catheters, vascular grafts, intraaortic balloon pumps, heart valves, cardiovascular sutures, total artificial hearts and ventricular assist pumps, extracorporeal devices such as blood oxygenators, blood filters, hemodialysis units, hemoperfusion units, plasmapheresis units, hybrid artificial organs such as pancreas or liver and artificial lungs and filters adapted for deployment in a blood vessel in order to trap emboli.

43. A composition according to claim 41, wherein the device provides a polymeric surface selected from the group consisting of polyurethane and its copolymers, silicone and its copolymers, ethylene vinyl-acetate, thermoplastic elastomers, polyvinyl chloride, polyolefins, cellulosics, polyamides, polyesters, polysulfones, polytetrafluorethylenes, polycarbonates, acrylonitrile butadiene styrene copolymers, acrylics, polylactic acid, polyglycolic acid, polycaprolactone, polylactic acid-polyethylene oxide copolymers, cellulose, collagens, and chitins.

44. A composition according to claim 41, wherein the device provides a surface selected from the group consisting of titanium/titanium alloys, TiNi, aluminum oxide, platinum/platinum alloys, stainless steels, pyrolytic carbon, silver, glassy carbon, polyurethanes, polycarbonates, silicone elastomers, polyolefins, polyvinyl chlorides, polyethers, polyesters, nylons, polyvinyl pyrrolidones, polyacrylates polymethacrylates, n-butyl cyanoacrylate, polyvinyl alcohols, polyisoprenes, rubber, cellulosics, polyvinylidene fluoride, polytetrafluoroethylene, ethylene tetrafluoroethylene copolymer, acrylonitrile butadiene ethylene, polyamide, polyimide, styrene acrylonitrile, hydroxyapatite, bone, skin, teeth, collagen, laminin, elastin, fibrin, wood, cellulose, compressed carbon and glass.

45. A crosslinked composition according to claim 21 wherein the polyether monomer comprises an alkoxy (poly)alkyleneglycol (meth)acrylate, the carboxylic acid-containing monomer is selected from carboxyl substituted ethylene compounds, the photoderivatized monomer is selected from the group consisting of N-[3-(4-benzoylbenzoamido)propyl] methacrylamide, 9-vinyl anthracene, and 9-anthracenylmethyl methacrylate, and the hydrophilic monomer is selected from the group consisting of acrylamide, N-vinylpyrrolidone, methacrylamide, and acrylamido propanesulfonic acid (AMPS).

46. A crosslinked composition according to claim 45 wherein the medicament is selected from the group consisting of gene therapy agents selected from therapeutic nucleic acids and nucleic acids encoding therapeutic gene products, antibiotics selected from penicillin, tetracycline, chloramphenicol, minocycline, doxycycline, vancomycin, bacitracin, kanamycin, neomycin, gentamycin, erytliromycin and cephalosporins and antiseptics selected from silver sulfadiazine, chlorhexidine, glutaraldehyde, peracetic acid, sodium hypochlorite, phenols, phenolic compounds, iodophor compounds, quaternary ammonium compounds, and chlorine compounds and the device is selected from the group consisting of catheters, implantable vascular access ports, blood storage bags, vascular stents, blood tubing, central venous catheters, arterial catheters, vascular grafts, intraaortic balloon pumps, heart valves, cardiovascular sutures, total artificial hearts and ventricular assist pumps, extracorporeal devices such as blood oxygenators, blood filters, hemodialysis units, hemoperfusion units, plasmapheresis units, hybrid artificial organs such as pancreas or liver and artificial lungs and filters adapted for deployment in a blood vessel in order to trap emboli.

47. A crosslinked composition according to claim 45, wherein the device provides a polymeric surface selected from the group consisting of polyurethane and its copolymers, silicone and its copolymers, ethylene vinyl-acetate, thermoplastic elastomers, polyvinyl chloride, polyolefins, cellulosics, polyamides, polyesters, polysulfones, polytetrafluorethylenes, polycarbonates, acrylonitrile butadiene styrene copolymers, acrylics, polylactic acid, polyglycolic acid, polycaprolactone, polylactic acid-polyethylene oxide copolymers, cellulose, collagens, and chitins.

48. A crosslinked composition according to claim 45, wherein the device provides a surface selected from the group consisting of titanium/titanium alloys, TiNi, aluminum oxide, platinum/platinum alloys, stainless steels, pyrolytic carbon, silver, glassy carbon, polyurethanes, polycarbonates, silicone elastomers, polyolefins, polyvinyl chlorides, polyethers, polyesters, nylons, polyvinyl pyrrolidones, polyacrylates polymethacrylates, n-butyl cyanoacrylate, polyvinyl alcohols, polyisoprenes, rubber, cellulosics, polyvinylidene fluoride, polytetrafluoroethylene, ethylene tetrafluoroethylene copolymer, acrylonitrile butadiene ethylene, polyamide, polyimide, styrene acrylonitrile, hydroxyapatite, bone, skin, teeth, collagen, laminin, elastin, fibrin, wood, cellulose, compressed carbon and glass.

49. The coating composition of claim 1, further comprising about 0.1 to about 10 mole % of a photoderivatized monomer.

* * * * *